(12) United States Patent
Sugiyama et al.

(10) Patent No.: US 9,851,356 B2
(45) Date of Patent: Dec. 26, 2017

(54) METHOD FOR MEASURING ANTI-WT1 ANTIBODY

(75) Inventors: Haruo Sugiyama, Minoo (JP); Yusuke Oji, Suita (JP); Kiyonori Katsuragi, Osaka (JP); Hideaki Tanaka, Osaka (JP); Shinji Sogo, Osaka (JP); Yoshihiro Goto, Osaka (JP); Yasukazu Ohmoto, Osaka (JP); Husako Iwata, Osaka (JP)

(73) Assignees: INTERNATIONAL INSTITUTE OF CANCER IMMUNOLOGY, INC., Suita-shi (JP); OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/239,449

(22) PCT Filed: Sep. 13, 2012

(86) PCT No.: PCT/JP2012/073512
§ 371 (c)(1),
(2), (4) Date: Feb. 18, 2014

(87) PCT Pub. No.: WO2013/039166
PCT Pub. Date: Mar. 21, 2013

(65) Prior Publication Data
US 2014/0227799 A1    Aug. 14, 2014

(30) Foreign Application Priority Data
Sep. 14, 2011 (JP) ................ 2011-200620

(51) Int. Cl.
G01N 33/53 (2006.01)
G01N 33/574 (2006.01)
C07K 14/82 (2006.01)
A61K 39/00 (2006.01)

(52) U.S. Cl.
CPC ........ *G01N 33/574* (2013.01); *A61K 39/0011* (2013.01); *C07K 14/82* (2013.01); *G01N 33/57426* (2013.01); *G01N 33/57488* (2013.01)

(58) Field of Classification Search
None
See application file for complete search history.

(56) References Cited

U.S. PATENT DOCUMENTS

| | | | |
|---|---|---|---|
| 7,063,854 B1 * | 6/2006 | Gaiger et al. | 424/277.1 |
| 7,824,865 B2 * | 11/2010 | Sugiyama | 435/7.1 |
| 2003/0138863 A1 | 7/2003 | Sugiyama | |
| 2005/0148037 A1 | 7/2005 | Sugiyama | |
| 2011/0124123 A1 * | 5/2011 | Sugiyama | 436/501 |

FOREIGN PATENT DOCUMENTS

| | | |
|---|---|---|
| CN | 1505526 A | 6/2004 |
| CN | 1671733 A | 9/2005 |
| CN | 101384716 A | 3/2009 |
| CN | 101573448 A | 11/2009 |
| CN | 101622344 A | 1/2010 |
| CN | 101888852 A | 11/2010 |
| EP | 1 288 661 A1 | 3/2003 |
| JP | 2002 48793 | 2/2002 |
| WO | WO 2010/123065 A1 | 10/2010 |

OTHER PUBLICATIONS

Oji et al (Int J Cancer, 2009, 125:381-387).*
Ichinohasama, R. et al., "Sensitive immunohistochemical detection of WT1 protein in tumors with anti-WT1 antibody against WT1 235 peptide", Cancer Science, vol. 101, No. 5, pp. 1089-1092, (May 2010).
Oka, Y. et al., "Development of cancer immunotherapy targeting WT1 gene product", Protein, Nucleic Acid and Enzyme, vol. 48, No. 11, pp. 1663-1670, (2003) (with partial English translation).
Inoue, K. et al., "WT1 as a New Prognostic Factor and a New Marker for the Detection of Minimal Residual Disease in Acute Leukemia", Blood, vol. 84, No. 9, pp. 3071-3079, (Nov. 1, 1994).
Oji, Y. et al., "Overexpression of the Wilms' Tumor Gene WT1 in De Novo Lung Cancers", Int. J. Cancer, vol. 100, pp. 297-303, (2002).
Miyoshi, Y. et al., "High Expression of Wilms' Tumor Suppressor Gene Predicts Poor Prognosis in Breast Cancer Patients", Cliical Cancer Research, vol. 8, pp. 1167-1171, (May 2002).
Haber, D. A. et al., "Alternative splicing and genomic structure of the Wilms tumor gene WT1", Proc. Natl. Acad. Sci., vol. 88, pp. 9618-9622, (Nov. 1991).
Madden, S. L. et al., "Transcriptional Repression Mediated by the WT1 Wilms Tumor Gene Product", Science, vol. 253, pp. 1550-1553, (1991).
Ellsseeva, O. A. et al., "Humoral immune responses against Wilms tumor gene WT1 product in patients with hematopoietic malignancies", Blood, vol. 99, No. 9, pp. 3272-3279, (May 1, 2002).
Oji, Y. et al., "WT1 IgG antibody for early detection of nonsmall cell lung cancer and as its prognostic factor", Int. J. Cancer., vol. 125, pp. 381-387, (2009).

(Continued)

*Primary Examiner* — Laura B Goddard
(74) *Attorney, Agent, or Firm* — Oblon, McClelland, Maier, Neustadt, L.L.P.

(57) ABSTRACT

Provided is an invention relating to a method for measuring an anti-WT1 antibody in a sample allowing measurement and evaluation of the anti-WT1 antibody with higher accuracy and to use of the method. The method for measuring an anti-WT1 antibody in a sample includes using a polypeptide having antigenicity to the anti-WT1 antibody selected from a polypeptide comprising the amino acid sequence of positions 294-449 in SEQ ID NO: 1, a partial polypeptide of the polypeptide, and a polypeptide including an amino acid sequence having deletion, substitution, or addition of one to several amino acids in the amino acid sequence constituting each of these polypeptides and/or a polypeptide having antigenicity to the anti-WT1 antibody selected from a polypeptide comprising the amino acid sequence of positions 181-324 in SEQ ID NO: 1, a partial polypeptide of the polypeptide, and a polypeptide including an amino acid sequence having deletion, substitution, or addition of one to several amino acids in the amino acid sequence constituting each of these polypeptides.

10 Claims, 12 Drawing Sheets

(56) References Cited

OTHER PUBLICATIONS

Tamura, H. et al., "Prognostic significance of WT1 mRNA and anti-WT1 antibody levels in peripheral blood in patients with myelodysplastic syndromes", Leukemia Research, vol. 34, pp. 986-990, (2010).
International Search Report dated Dec. 18, 2012 in PCT/JP12/073512 dated Sep. 13, 2012.
Written Opinion of the International Searching Authority dated Dec. 18, 2012 in PCT/JP12/073512 dated Sep. 13, 2012.
Extended European Search Report dated Jun. 1, 2015 in Patent Application No. 12832236.9.
Alexander Gaiger, et al., "WT1-specific Serum Antibodies in Patients with Leukemia" Clinical Cancer Research, vol. 7, XP055189591, 2001, pp. 761s-765s and cover page.
Peter G. Maslak, et al., "Vaccination with synthetic analog peptides derived from WT1 oncoprotein induces T-cell responses in patients with complete remission from acute myeloid leukemia" Clinical Trials and Observations, Blood, vol. 116, No. 2, XP055190150, 2010, pp. 171-179 and cover page.
Hiroaki Shimamoto, et al., "WT1 peptide vaccine immunotherapy for recurrent glioblastoma: An evaluation of therapy effect by means of C-11 methionine and F-18 FDG PET" The Journal of Nuclear Medicine, vol. 47, XP055190197, 2006, 2 pages.
Mariko Yokouchi, et al., "Pathogenic Epitopes of Autoantibodies in Pemphigus Reside in the Amino-Terminal Adhesive Region of Desmogleins Which Are Unmasked by Proteolytic Processing of Prosequence" The Journal of Investigative Dermatology, vol. 129, No. 9, XP003029229, 2009, pp. 1-24.
Office Action dated Dec. 7, 2016 in Russian Patent Application No. 2014114532 (with English translation).
Robert Koesters, et al., "WT1 is a tumor-associated antigen in colon cancer that can be recognized by in vitro stimulated cytotoxic T cells", Int. J. Cancer, vol. 109, 2004, pp. 385-392.
Jens Schittenhelm, et al., "WT1 expression in normal and neoplastic cranial and peripheral nerves is independent of grade of malignancy", Cancer Biomarkers, vol. 7, No. 2, DOI: 10.3233/CBM-2010-0149, 2010, 17 Pages.
Combined Office Action and Search Report dated Feb. 2, 2015 in Chinese Patent Application No. 201280044353.0 (with English Translation of Category of Cited Documents).

* cited by examiner

METHOD FOR MEASURING ANTI-WT1 ANTIBODY

TECHNICAL FIELD

The present invention relates to a method for measuring an anti-WT1 antibody in a sample using a WT1 fragment.

BACKGROUND ART

A WT1 gene (Wilms tumor gene) is a zinc finger transcription factor isolated as a responsible gene for Wilms tumor. Abnormally high expression of the WT1 gene was then confirmed in acute myeloid leukemia and also in various solid cancers (Non Patent Documents 1 to 3), and application of a WT1 protein as a peptide vaccine has been tried.

In recent years, it has been revealed that the WT1 protein has a structure including a repression domain, an activation domain, and a zinc finger domain, which is a DNA-binding domain, and regulates gene expression by binding to an early growth response protein 1 (EGR-1) region. A function as a tumor suppressor gene has also been reported (Non Patent Documents 4 and 5).

In addition, the presence of autoantibodies to the WT1 protein has been revealed. It has been reported that the titer of autoantibody against the WT1 protein is particularly high in blood of hematological cancer or lung cancer (small cell cancer) patients (Non Patent Documents 6 to 8). Higher expression of WT1 mRNA tends to cause poor prognosis. In contrast, it has been reported that a higher blood level of an anti-WT1 antibody tends to cause good prognosis (Non Patent Document 7). Accordingly, it is believed that accurate measurement of the anti-WT1 antibody in patient blood is useful for selection of a method of treatment or monitoring of treatment progress. For example, measurement of an anti-WT1 antibody using a WT1 protein containing the repression domain and the activation domain but lacking the zinc finger as an antigen has been reported (Patent Documents 1 and 2).

However, the mechanism by which an in vivo protein becomes to be recognized as a foreign substance and induces production of an autoantibody thereto is still unclear. In addition, the concentration of the antibody is very low, and a method for detecting an autoantibody with high sensitivity has not been established. Also regarding the anti-WT1 antibody, there is a problem that the known method using a WT1 protein antigen cannot necessarily accurately evaluate the antibody because of the narrow titer distribution of the detected antibody.

CITATION LIST

Patent Document

[Patent Document 1] JP-A-2002-48793
[Patent Document 2] JP-A-2006-267124

Non Patent Document

[Non Patent Document 1] Inoue K, Sugiyama H, Ogawa H, et al., WT1 as a new prognostic factor and new marker for the detection of minimal residual disease in acute leukemia, Blood 1994, 84: 3071-9

[Non Patent Document 2] Oji Y, Miyoshi S, Maeda H, et al., Overexpression of the Wilms' tumor gene WT1 in de novo lung cancers, Int J Cancer 2002, 100: 297-303

[Non Patent Document 3] Miyoshi Y, Ando A, Egawa C, et al., High expression of Wilms' tumor suppressor gene predicts poor prognosis in breast cancer patients, Clin Cancer Res 2002, 8: 1167-71

[Non Patent Document 4] Haber D A, Sohn R L, Buckler A J, et al., Alternative splicing and genomic structure of the Wilms' tumor gene WT1, Proc Natl Acad Sci USA 1991, 88: 9618

[Non Patent Document 5] Madden S L, Cook D M, Morris J F, et al., Transcriptional repression mediated by the WTI Wilms tumor gene product, Science 1991, 253: 1550

[Non Patent Document 6] Olga AEl, Oka Y, Tsuboi A, et al., Humoral immune responses against Wilms tumor gene WT1 product in patients with hematopoietic malignancies, Blood 2002, 99: 3272-3279

[Non Patent Document 7] Oji Y, Kitamura Y, Kamino K, et al., WT1 IgG antibody for early detection of nonsmall cell lung cancer and as its prognostic factor, Int J Cancer 2009, 125: 381-7

[Non Patent Document 8] Tamura H, Dan K, Yokose N, et al., Prognostic significance of WT1 mRNA and anti-WT1 antibody levels in peripheral blood in patients with myelodysplastic syndromes, Leukemia Res 2010, 34: 986-990

SUMMARY OF THE INVENTION

Problems to be Solved by the Invention

It is an object of the present invention to provide a method for measuring an anti-WT1 antibody that enables more accurate measurement and evaluation of the anti-WT1 antibody in a WT1-associated disease patient and use of the method.

Means for Solving the Problems

The present inventors have investigated detection of an anti-WT1 antibody in blood of WT1-associated disease patients and have found that an in vivo autoantibody to an antigen is produced when the antigen recognized by the autoantibody is conformationally modified to expose an epitope site to the surface and is thereby recognized as a foreign substance. The inventors have also found that the major epitopes of WT1 are the central region (amino acid numbers: 181-324) and the C-terminal region (amino acid numbers: 294-449) of the amino acid sequence (SEQ ID NO: 1) constituting the human WT1 protein and that the anti-WT1 antibody titer in measurement of the anti-WT1 antibody using a polypeptide fragment corresponding to the C-terminal region (zinc finger region), a DNA biding domain of WT1, as an antigen particularly shows a high correlation with that in the measurement using the full-length WT1 as an antigen. The inventors further have found that in comparison between the titer distribution of antibodies in healthy subjects and those in cancer patients, the titer distribution of antibodies in the cancer patients is broader than that in the healthy subjects to show a significant difference, which allows accurate and sensitive determination of a high titer group of the anti-WT1 antibody, such as cancer patients.

Accordingly, the present invention relates to the following aspects 1) to 9):

1) A method for measuring an anti-WT1 antibody in a sample, the method comprising using a polypeptide having antigenicity to the anti-WT1 antibody selected from a polypeptide comprising the amino acid sequence of positions 294-449 in SEQ ID NO: 1, a partial polypeptide of the polypeptide, and a polypeptide including an amino acid sequence having deletion, substitution, or addition of one to several amino acids in the amino acid sequence constituting each of these polypeptides and/or a polypeptide having antigenicity to the anti-WT1 antibody selected from a polypeptide comprising the amino acid sequence of positions 181-324 in SEQ ID NO: 1, a partial polypeptide of the polypeptide, and a polypeptide including an amino acid sequence having deletion, substitution, or addition of one to several amino acids in the amino acid sequence constituting each of these polypeptides;

2) The method according to aspect 1), wherein a concentration of the antibody is measured by immobilizing at least one of the polypeptides to a solid phase and detecting a reaction product between the immobilized polypeptide or polypeptides and an anti-WT1 antibody present in a sample;

3) A method for diagnosing a WT1-associated disease, the method comprising using a polypeptide having antigenicity to an anti-WT1 antibody selected from a polypeptide comprising the amino acid sequence of positions 294-449 in SEQ ID NO: 1, a partial polypeptide of the polypeptide, and a polypeptide including an amino acid sequence having deletion, substitution, or addition of one to several amino acids in the amino acid sequence constituting each of these polypeptides and/or a polypeptide having antigenicity to the anti-WT1 antibody selected from a polypeptide comprising the amino acid sequence of positions 181-324 in SEQ ID NO: 1, a partial polypeptide of the polypeptide, and a polypeptide including an amino acid sequence having deletion, substitution, or addition of one to several amino acids in the amino acid sequence constituting each of these polypeptides;

4) The method according to aspect 3), which determines prognosis of leukemia;

5) A method for predicting a responder to or for therapeutic monitoring of WT1 vaccine therapy of cancer, the method comprising using a polypeptide having antigenicity to an anti-WT1 antibody selected from a polypeptide comprising the amino acid sequence of positions 294-449 in SEQ ID NO: 1, a partial polypeptide of the polypeptide, and a polypeptide including an amino acid sequence having deletion, substitution, or addition of one to several amino acids in the amino acid sequence constituting each of these polypeptides and/or a polypeptide having antigenicity to the anti-WT1 antibody selected from a polypeptide comprising the amino acid sequence of positions 181-324 in SEQ ID NO: 1, a partial polypeptide of the polypeptide, and a polypeptide including an amino acid sequence having deletion, substitution, or addition of one to several amino acids in the amino acid sequence constituting each of these polypeptides;

6) The method according to aspect 5), wherein the cancer is brain tumor or colon cancer;

7) A reagent for measuring an anti-WT1 antibody in a sample, the reagent comprising a polypeptide having antigenicity to an anti-WT1 antibody selected from a polypeptide comprising the amino acid sequence of positions 294-449 in SEQ ID NO: 1, a partial polypeptide of the polypeptide, and a polypeptide including an amino acid sequence having deletion, substitution, or addition of one to several amino acids in the amino acid sequence constituting each of these polypeptides and/or a polypeptide having antigenicity to the anti-WT1 antibody selected from a polypeptide comprising the amino acid sequence of positions 181-324 in SEQ ID NO: 1, a partial polypeptide of the polypeptide, and a polypeptide including an amino acid sequence having deletion, substitution, or addition of one to several amino acids in the amino acid sequence constituting each of these polypeptides;

8) A reagent for examining a WT1-associated disease, the reagent comprising a polypeptide having antigenicity to an anti-WT1 antibody selected from a polypeptide comprising the amino acid sequence of positions 294-449 in SEQ ID NO: 1, a partial polypeptide of the polypeptide, and a polypeptide including an amino acid sequence having deletion, substitution, or addition of one to several amino acids in the amino acid sequence constituting each of these polypeptides and/or a polypeptide having antigenicity to the anti-WT1 antibody selected from a polypeptide comprising the amino acid sequence of positions 181-324 in SEQ ID NO: 1, a partial polypeptide of the polypeptide, and a polypeptide including an amino acid sequence having deletion, substitution, or addition of one to several amino acids in the amino acid sequence constituting each of these polypeptides; and 9) A method for detecting an autoantibody, the method comprising modifying an in vivo protein such that an epitope site is exposed to the surface and using the modified protein as an antigen recognized by the autoantibody.

Effects of the Invention

The method for measuring an anti-WT1 antibody of the present invention can accurately and sensitively measure the anti-WT1 antibody in WT1-associated disease patients and therefore allows satisfactory detection of a variation in the anti-WT1 antibody titer. Accordingly, it is possible to easily and highly sensitively perform, for example, diagnosis of WT1-associated diseases, monitoring of therapeutic effects, determination of prognosis, prediction of a responder before vaccine therapy, and monitoring of response to vaccine therapy after the therapy.

3 antigen, No. 3, No. 7, and No. 9 are patient serum showing low titers of antibodies against Fr. 1 and Fr. 2 and high titers of antibody against Fr. 3, the white bars show the results in the presence of the Fr. 1 antigen, and the black bars show the results in the presence of the Fr. 2 antigen.

Figure 6:
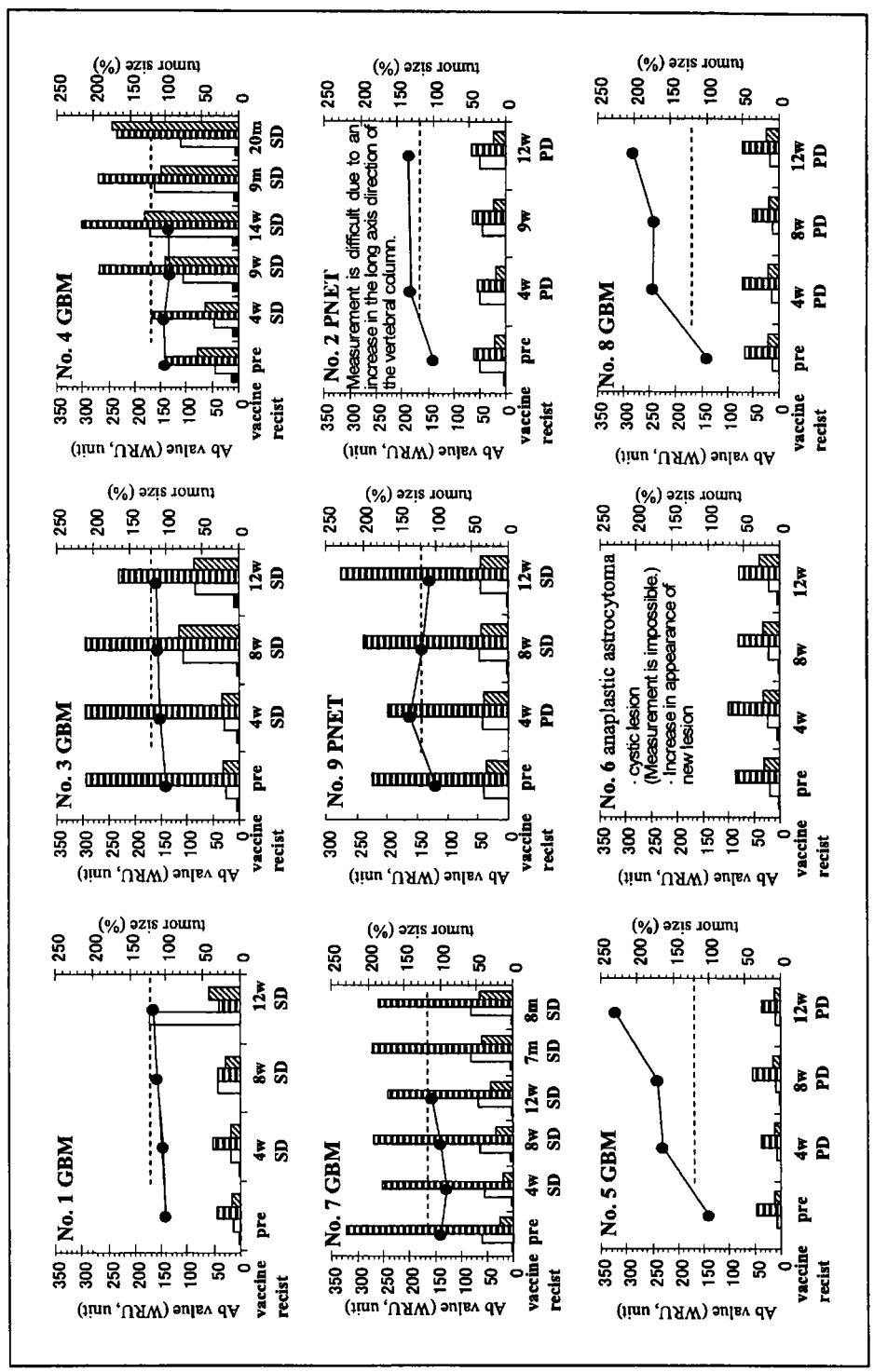

FIG. 6 includes graphs showing changes in the titer of IgG antibody against each antigen, wherein the black bars show changes in titer of the antibody against Fr. 1, the white bars show changes in titer of the antibody against Fr. 2, the horizontal line bars show changes in titer of the antibody against Fr. 3, the oblique line bars show changes in titer of the antibody against the full-length WT1 antigen, and the black circles show variations in tumor size measured by MRI.

Figure 7:
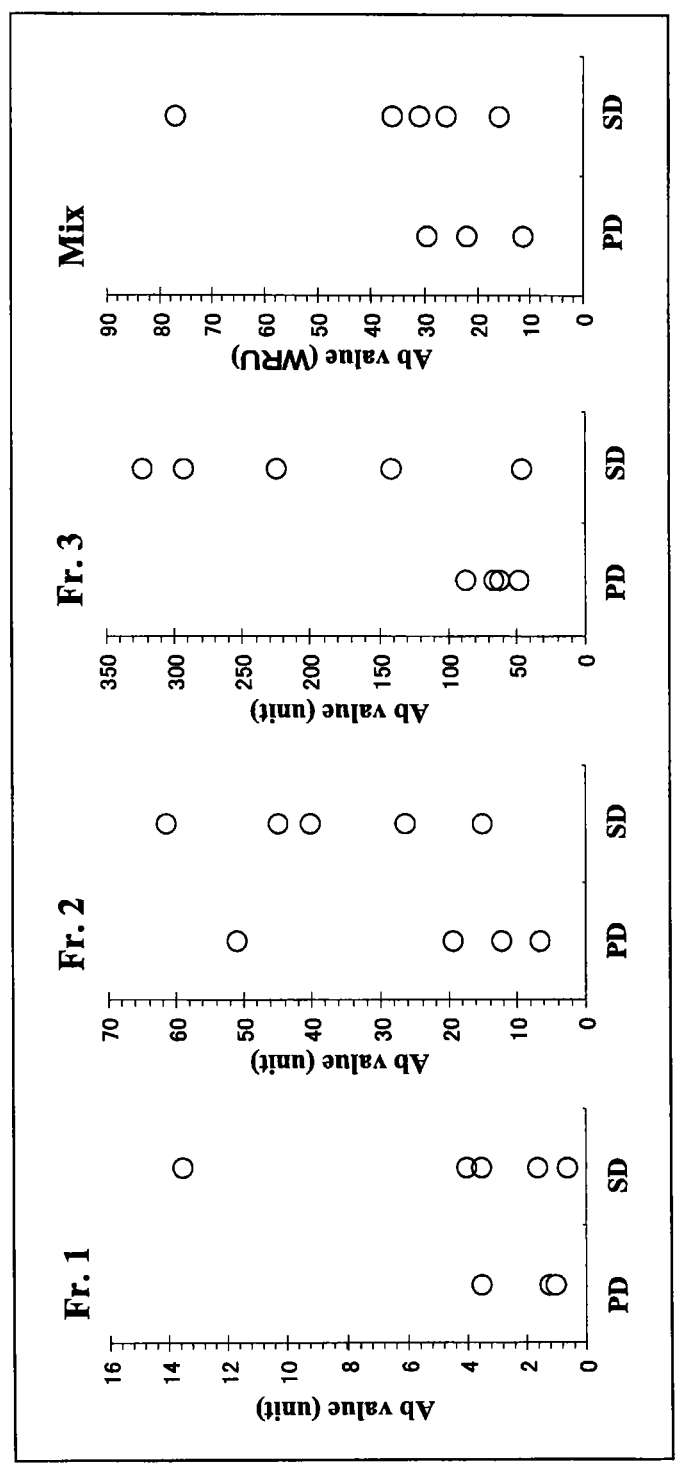

FIG. 7 includes graphs showing the results of comparison of IgG antibody titer before vaccination.

Figure 8:
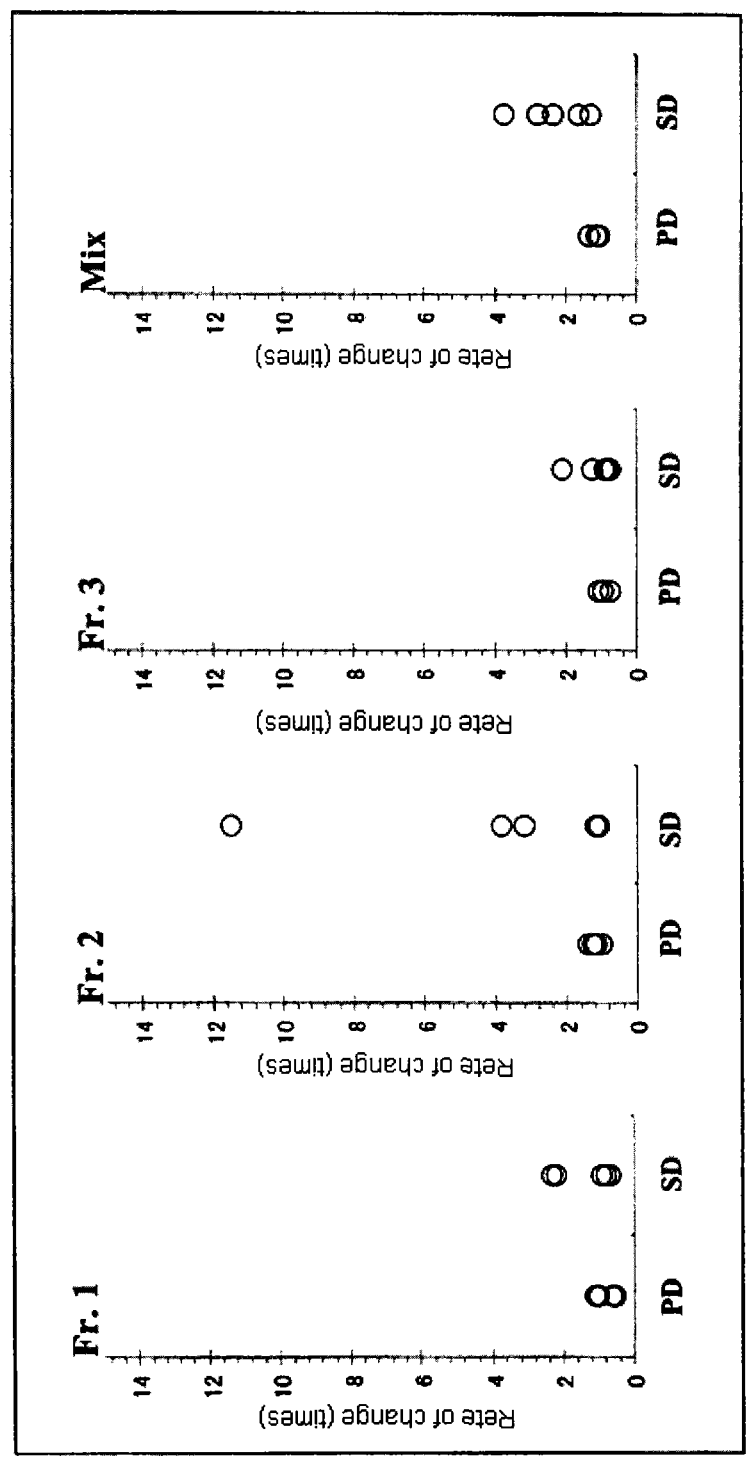

FIG. 8 includes graphs showing the results of comparison of IgG antibody titer after vaccination.

Figure 9:
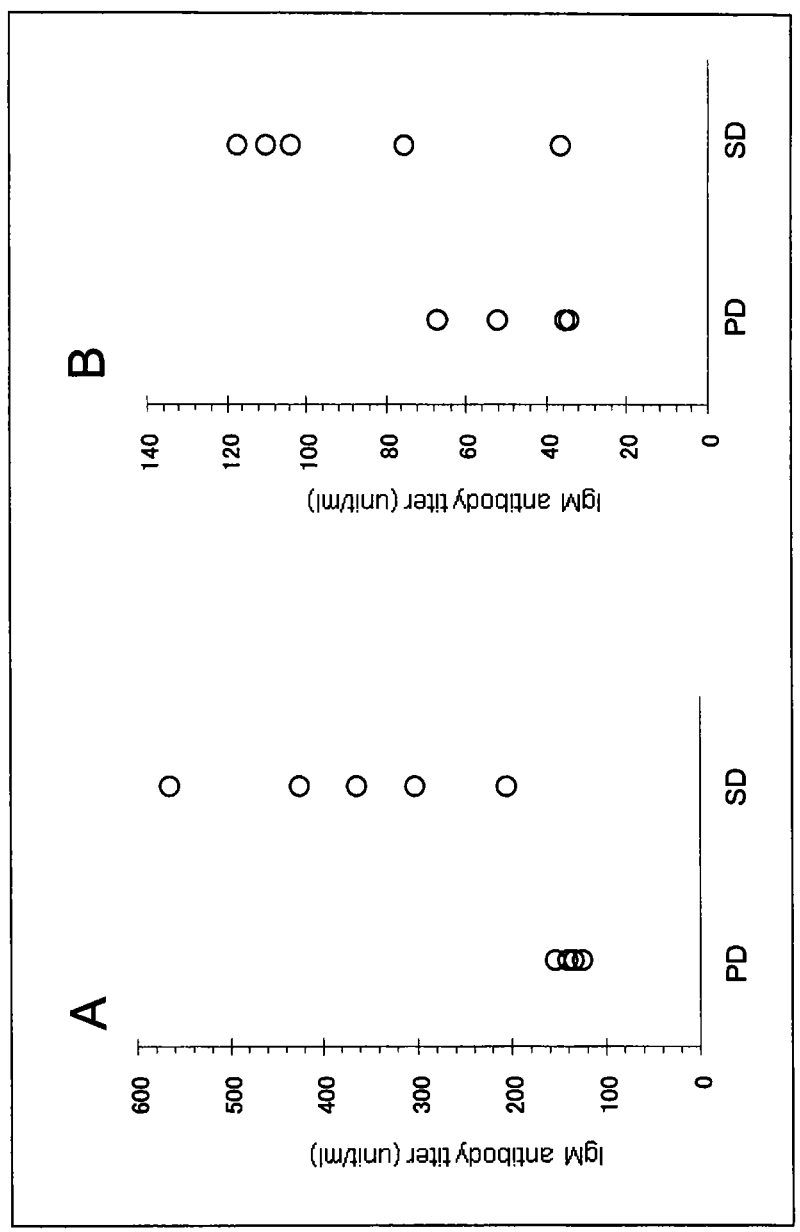

FIG. 9 includes graphs showing IgM antibody titers before vaccination, wherein A shows titers of IgM antibody against Fr. 2, and B shows the titers of IgM antibody against Fr. 3.

Figure 10:
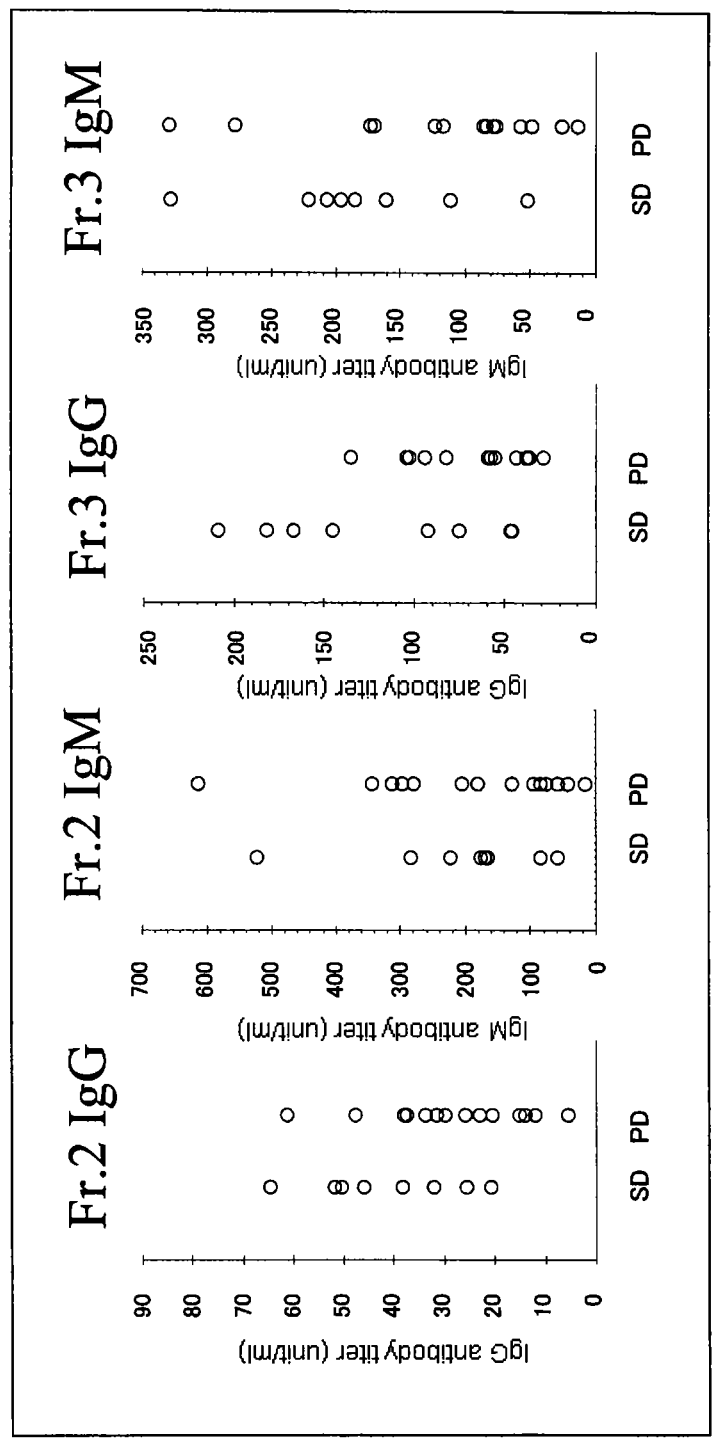

FIG. 10 includes graphs showing IgM and IgG antibody titers before vaccination.

Figure 11:
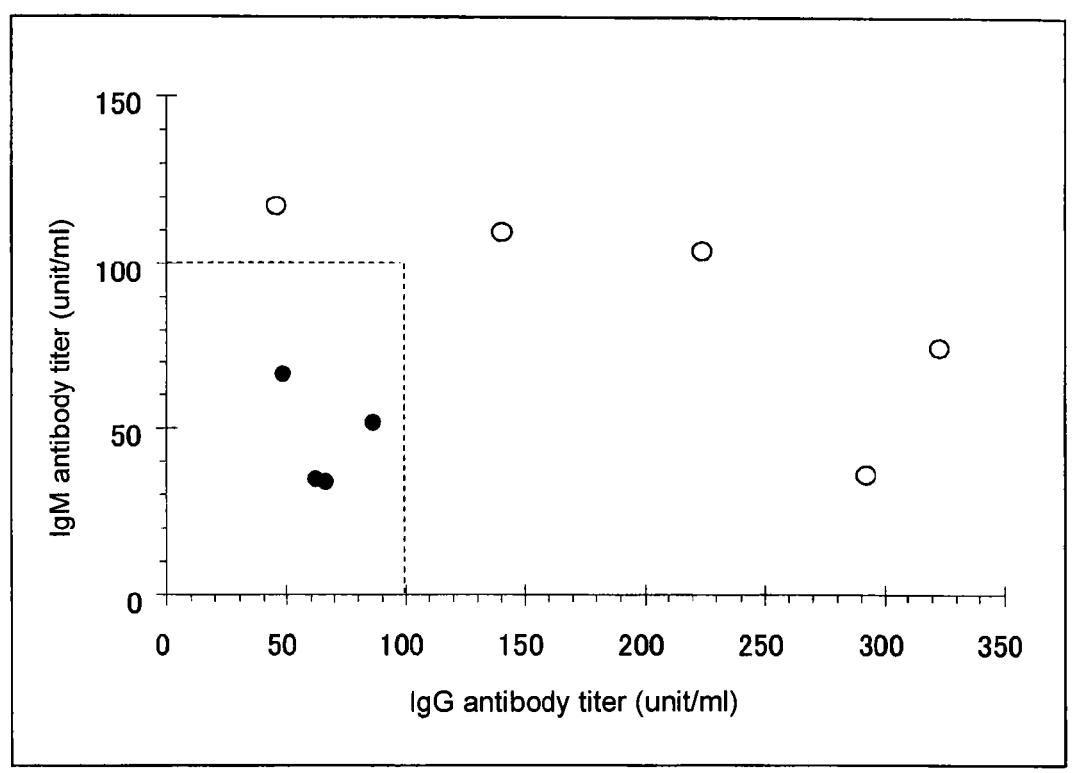

FIG. 11 is a graph showing IgM and IgG antibody titers in brain tumor patients, wherein the vertical axis shows IgM antibody titers, the horizontal axis shows IgG antibody titers, the open circles show the results of SD patients, the black circles show the results of PD patients, and the dotted line shows tentative reference values.

Figure 12:
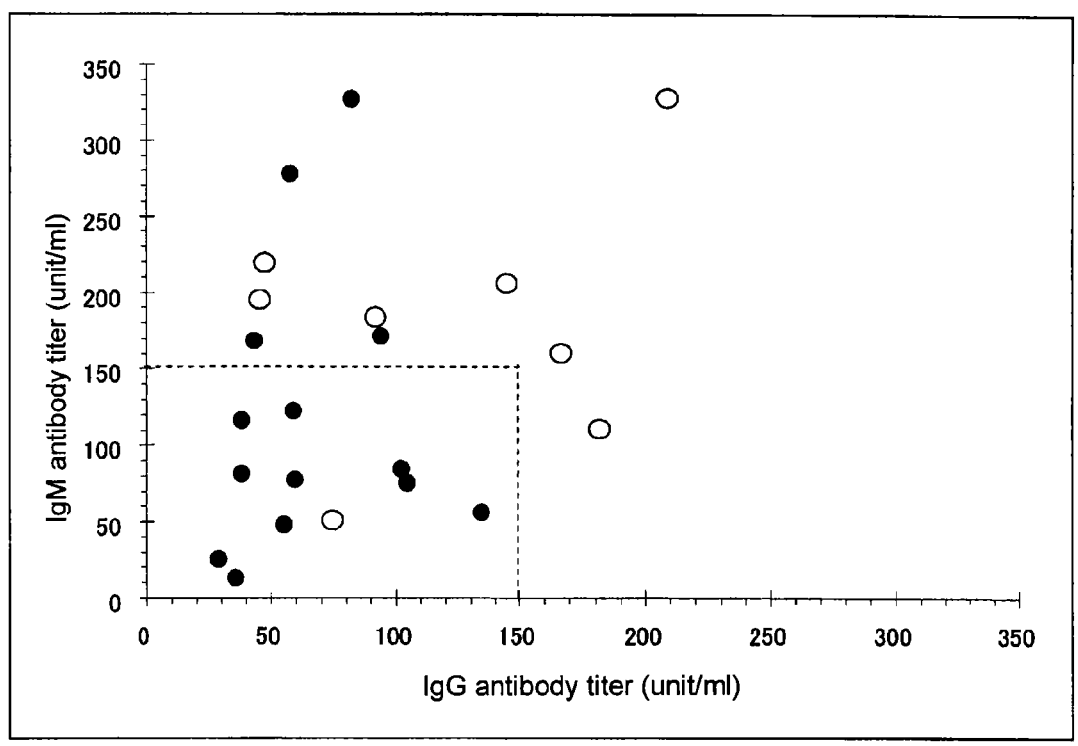

FIG. 12 is a graph showing IgM and IgG antibody titers in colon cancer patients, wherein the vertical axis shows IgM antibody titers, the horizontal axis shows IgG antibody titers, the open circles show the results of SD patients, the black circles show the results of PD patients, and the dotted line shows tentative reference values.

DESCRIPTION OF THE EMBODIMENTS

In the present invention, the anti-WT1 antibody refers to antibodies against a gene product of a zinc finger transcription factor WT1 isolated as a responsible gene for Wilms tumor (Wilms tumor gene), specifically, a human WT1 protein (SEQ ID NO: 1) consisting of 449 amino acids. Such antibodies include a variety of immunoglobulins such as IgG antibody, IgA antibody, and IgM antibody, and these antibodies are all encompassed in the present invention.

In vivo proteins are primarily not recognized as foreign substances by the immune system and therefore do not usually induce production of antibodies. The present inventors presumed that an autoantibody to an antigen is produced when the antigen recognized by the autoantibody is conformationally modified to expose an epitope site to the surface and is thereby recognized as a foreign substance. Consequently, it is believed that in order to prepare an antigen to be recognized by an autoantibody, an epitope site hidden in the molecule is required to be exposed to the surface by modifying the protein through, for example, genetic engineering for expressing a protein having partial deletion of the surface site, cleavage of peptide bond with a protease, treatment with an acid, an alkali, or a surfactant, thermal denaturation, or treatment with a chaotropic reagent such as urea or guanidine hydrochloride.

The present inventors, as shown in examples below, have investigated molecules of the WT1 protein that can be an antigen recognized by an autoantibody and have found that the major epitopes are the central region (amino acid numbers: 181-324) and the C-terminal region (amino acid numbers: 294-449) of the amino acid sequence (SEQ ID NO: 1) constituting the human WT1 protein and that use of a peptide at the C-terminal region as an antibody-detecting antigen can particularly increase the antibody detection sensitivity to be higher than that when a full-length WT1 antigen is used (Example 1) and that the reactivity of antibody with the C-terminal side region is inhibited by antigens of the N-terminal side region (amino acid numbers: 1-182) and the central region (Example 2) and have proved the above-mentioned points.

The polypeptide having antigenicity to an anti-WT1 antibody used in the method for measuring the anti-WT1 antibody of the present invention is selected from a polypeptide comprising the amino acid sequence of positions 294-449 in SEQ ID NO: 1, a polypeptide comprising the amino acid sequence of positions 181-324 in SEQ ID NO: 1, a polypeptide including an amino acid sequence having deletion, substitution, or addition of one to several amino acids in the amino acid sequence constituting each of these polypeptides, and partial polypeptides of these polypeptides.

The polypeptide comprising the amino acid sequence of positions 294-449 in SEQ ID NO: 1 corresponds to a zinc finger domain, which is a DNA-binding domain, in the WT1 protein and is also referred to as a C-terminal region in the present invention.

The polypeptide comprising the amino acid sequence of positions 181-324 in SEQ ID NO: 1 corresponds to a region between the N-terminal side region (amino acid numbers: 1-182) and the C-terminal region in the WT1 protein and is also referred to as a central region.

The antigen polypeptide is preferably the polypeptide comprising the amino acid sequence of positions 294-449 or the polypeptide comprising the amino acid sequence of positions 181-324 in SEQ ID NO: 1, but may be a partial polypeptide of the polypeptides or a polypeptide including an amino acid sequence having deletion, substitution, or addition of one to several amino acids in the amino acid sequence constituting each of these polypeptides as long as the antigen polypeptide has antigenicity to an anti-WT1 antibody and can detect the anti-WT1 antibody.

Examples of the partial polypeptide of the polypeptides include peptides each comprising 6 to 8, preferably 10 to 20, consecutive amino acids of the amino acid sequence of positions 294-449 or the amino acid sequence of positions 181-324 in SEQ ID NO: 1. Specific examples of the partial polypeptide include a polypeptide comprising the amino acid sequence of positions 294-449 in SEQ ID NO: 1, a polypeptide comprising the amino acid sequence of positions 348-449 in SEQ ID NO: 1, and a polypeptide comprising the amino acid sequence of positions 181-324 in SEQ ID NO: 1.

The polypeptide comprising the amino acid sequence of positions 294-449 and the polypeptide comprising the amino acid sequence of positions 181-324 of SEQ ID NO: 1 and partial polypeptides thereof may each have deletion, substitution, or addition of one to several amino acids in the amino acid sequence thereof as long as the polypeptide has antigenicity to an anti-WT1 antibody.

Throughout the specification, the number of amino acids that can be deleted, added, or substituted is one or more and is not particularly limited and is a number of amino acids that can be deleted, added, or substituted by a known method such as site-specific mutagenesis and is, for example, one to several tens, preferably one to twenty, more preferably one to ten, and even more preferably one to five.

Throughout the specification, deletion, addition, or substitution of one or more amino acid residues in an amino acid sequence means that one or more amino acid residues are deleted, added, or substituted in arbitrary one or more positions in the same amino acid sequence. The deletion, addition, or substitution may simultaneously occur, and the amino acid residues that are deleted, added, or substituted may be natural or non-natural amino acids.

The term "antigenicity to an anti-WT1 antibody" refers to antigenicity to an antibody recognizing a WT1 protein. Since the autoantibodies in WT1-associated disease patients are polyclonal antibodies, the antigen polypeptide itself of the present invention may have a plurality of reaction sites (epitopes).

The polypeptide used in the method of the present invention is at least one polypeptide selected from the above-mentioned polypeptides. In order to enhance the specificity and measurement sensitivity, a combination of a plurality of polypeptides may be used.

These polypeptides can be produced by a known genetic engineering using a WT1 gene, for example, the method described in the example below or a method in accordance with that or can also be produced by chemical synthesis.

The production of the polypeptide by genetic engineering using a WT1 gene can be performed by usual genetic recombination conventionally known. More specifically, a recombinant DNA capable of expressing a desired WT1 gene in a host cell is prepared, the recombinant DNA is introduced into host cells for transformation, and the transformant is cultured. The transformant can produce a desired polypeptide intracellularly or extracellularly as an expression product of the transformant.

Each operation employed here, for example, chemical synthesis of partial genes, enzyme treatment for cleavage, deletion, addition, or bonding thereof, isolation, purification, selection, and other treatment thereof, introduction of a recombinant DNA into a host cell, and culture of the transformant can be performed in accordance with usual methods (see, for example, "Bunshi Idengaku Jikken-ho (Molecular Genetics Experimental Method)", Kyoritsu Shuppan Co., Ltd., published in 1993; "PCR Technology", Takara Shuzo Co., Ltd., published in 1990; Science, 224, 1431 (1984); Biochem. Biophys. Res. Comm., 130, 692 (1985); Proc. Natl. Acad. Sci. USA., 80, 5990 (1983); Molecular Cloning, by T. Maniatis et al., Cold Spring Harbor Laboratory (1982)).

The polypeptide can also be optionally isolated and purified from the expression product by various separation procedures utilizing the physical and chemical properties of the polypeptide (see, for example, "Biochemistry Data Book II", pp. 1175-1259, First edition, First printing, Jun. 23, 1980, published by Tokyo Kagaku Dojin, Co., Ltd.).

The sample in the present invention is a sample derived from a WT1-associated disease patient or a WT1-associated disease patient after treatment, and unlimited examples thereof include body fluids such as blood and urine, which are known to generally contain antibodies.

Examples of the WT1-associated disease include various diseases known as WT1-associated diseases, such as leukemia, solid cancers, and myelodysplastic syndrome and also include WT1-associated diseases that may be found in future.

In the method for measuring an anti-WT1 antibody of the present invention, measurement of the anti-WT1 antibody (the concentration of the antibody) can be performed by immunoassay using the above-mentioned polypeptide. The immunoassay may be any known immunoassay, and examples thereof include radioimmunoassay (RIA), enzyme immunoassay (EIA or ELISA), fluoroimmunoassay (FIA), indirect fluorescence assay, luminescent immunoassay, physicochemical assays (TIA, LAPIA, and PCIA), and Western blotting. ELISA is preferably used.

ELISA is a method performed by reacting an antibody to an antigen immobilized to a solid phase, further reacting a secondary antibody labeled with an enzyme such as peroxidase or alkaline phosphatase to the antibody bound to the antigen, and then measuring the enzyme label by an appropriate process. Examples of the ELISA include a competitive method and a sandwich method. The sandwich method (solid-phase sandwich method) is particularly preferred.

The solid-phase sandwich method is performed by, for example, as follows: A polypeptide of the present invention is immobilized to a solid phase, and a sample to be measured is added thereto. As a result, an antigen-antibody reaction occurs between the solid-phase-immobilized antigen and an antibody in the sample, and thereby an anti-WT1 antibody present in the sample binds to the solid-phased antigen. Subsequently, the bound antibody is detected with an antibody detection reagent to measure the anti-WT1 antibody present in the sample.

Alternatively, the antibody detection reagent may be immobilized to a solid phase. An objective anti-WT1 antibody present in a sample can be detected or measured by capturing antibodies in the sample, then adding a polypeptide of the present invention to the reagent so as to bind to the anti-WT1 antibody among the captured antibodies, and further binding a labeled specific antibody to the antigen.

Selection of each process and modification thereof in these measuring methods are well known to those skilled in the art and are not particularly limited in the present invention, and any method can be employed (see, for example, "Rinsho Kensa-ho Teiyo (Clinical Examination Handbook)", Kanehara & Co., Ltd., 1995).

For example, the solid phase used in the solid-phase method may be an insoluble inactive carrier that is usually used widely. Examples of the carrier include sticks, beads, microplates, and test tubes made of various materials such as glass, cellulose powder, sephadex, sepharose, polystyrene, filter paper, carboxymethyl cellulose, ion exchange resins, dextran, plastic films, plastic tubes, nylon, glass beads, silk, polyamine-methyl vinyl ether-maleic acid copolymers, amino acid copolymers, and ethylene-maleic acid copolymers.

The immobilization of an antigen or an antibody is not particularly limited and may be physical bonding or chemical bonding. Typical examples of the immobilization include chemical binding methods such as covalent bonding methods, e.g., diazo methods, peptide methods (acid amide derivative method, carboxyl chloride resin method, carbodiimide resin method, maleic anhydride derivative method, isocyanate derivative method, bromocyan activated polysaccharide method, cellulose carbonate derivative method, condensing reagent method, etc.), alkylation method, crosslinking reagent coupling method (using, for example, glutaraldehyde or hexamethylene isocyanate as the crosslinking reagent), and Ugi reaction coupling method; ionic binding methods using supports such as ion exchange resins; and physical adsorption methods using porous glass supports such as glass beads.

The labeling reagent in each measurement system is not particularly limited, and any conventionally known or expected to come into use in future can be used. Specifically, those usually used in immunoassay can be used without any limitation, and examples thereof include radioisotopes;

enzymes such as alkaline phosphatase (ALP) and peroxidase (PDX); fluorescent substances such as fluorescein isothiocyanate (FITC) and tetramethylrhodamine isothiocyanate (RITC); and 1N-(2,2,6,6-tetramethyl-1-oxyl-4-piperidyl)-5N-(aspartate)-2,4-dinitrobenzene (TOPA).

Examples of the enzyme labeling material for enzyme labeling include, in addition to those mentioned above, microperoxidase, chymotripsinogen, procarboxypeptidase, glyceroaldehyde-3-phosphate dehydrogenase, amylase, phosphorylase, D-Nase, and P-Nase. Labeling using these labeling materials may be performed according to a known method (see, for example, "Monoclonal antibody", Tatsuo Iwasaki, et al., Kodansya Scientific, 1984; "Enzyme Immunoassay", 2nd edition, Eiji Ishikawa, et al., Igaku Shoin, 1982).

The enzyme activity can be measured by a known method depending on the type of the enzyme used. For example, in a case of using peroxidase as a labeling enzyme, ABTSJ (2,2'-azino-bis(3'-ethylbenzthiazoline sulfonic acid) is used as the substrate; in a case of using alkaline phosphatase, p-nitrophenyl phosphate is used as the substrate, and the decomposition of each substrate is measured with, for example, a spectrophotometer (See, for example, "Enzyme Immunoassay", 2nd edition, Eiji Ishikawa, et al., Igaku Shoin, 1982).

When a radioisotope or fluorescent material is used instead of the enzyme label as a marker, the marker can also be measured by a known method.

In the measurement system, any solvent that is usually used and does not adversely affect the reaction can be used. Specifically, a buffer solution having a pH of about 5 to 9, such as a citrate buffer solution, a phosphate buffer solution, a tris-hydrochloric acid buffer solution, or an acetate buffer solution can be preferably used.

Immune reaction (binding) conditions are not particularly limited, and usual conditions that are used in these assays are employed. In general, a reaction may be performed at a temperature of 45° C. or less, preferably about 4 to 40° C., for about 1 to 40 hours.

Accordingly, in the method using the polypeptide of the present invention as an antigen, an anti-WT1 antibody in a WT1-associated disease patient can be accurately and sensitively measured, and a variation in the anti-WT1 antibody titer can be satisfactorily detected.

The concentrations of the anti-WT1 antibody in WT1-associated disease patients are significantly increased compared to those in healthy subjects and are reduced by treatment of the patients. Accordingly, it is possible to determine the presence, treatment progress, and prognosis of a WT1-associated disease using the concentration of the anti-WT1 antibody, preferably the change of the concentration with time, as a clinical index. For example, the anti-WT1 antibody disappears when a WT1-associated disease such as leukemia has completely remitted. The maintenance of the complete remission state can be confirmed by investigating the disappearance of this antibody over time.

Detection of an anti-WT1 antibody in a WT1-associated disease patient, i.e., identification of an anti-WT1 antibody positive patient means that humoral immune response to WT1 is caused in the patient. Accordingly, the detection itself of an anti-WT1 antibody is useful for determining or diagnosing the immune response ability of the patient in the WT1-associated disease. Patients showing immune response to WT1 may have better prognosis, because of the high immune response, compared to patients not showing immune response. Such determination or diagnosis can be an index for determining the prognosis of a WT1-associated disease.

Accordingly, the method for measuring an anti-WT1 antibody of the present invention is useful for determining the presence, treatment progress, and prognosis of a WT1-associated disease, in particular, for examination or diagnosis of immune response ability (to cancer) of various cancer patients.

The method for measuring an anti-WT1 antibody of the present invention can be applied to prediction of a responder to WT1 vaccine therapy of cancer before the therapy or to monitoring of response to the therapy after the therapy. For example, a patient of cancer, such as brain tumor or colon cancer, having a high titer of IgG antibody or of IgM antibody against a peptide in the C-terminal side region (e.g., a polypeptide comprising the amino acid sequence of positions 294-449 in SEQ ID NO: 1) or a high titer of IgM antibody against a peptide in a central region (e.g., a polypeptide comprising the amino acid sequence of positions 181-324 in SEQ ID NO: 1) before administration of a WT1 vaccine can be expected to obtain high therapeutic effect by the WT1 vaccine. Furthermore, in a responder, the titer of IgG antibody to the peptide of the central region increases after WT1 vaccine administration, and a tendency of a slight increase in the titer of IgG antibody to the peptide of the C-terminal side region is also recognized. These results demonstrate that therapeutic response can be monitored using the change in the titer of IgG antibody to the peptide of the central region or the C-terminal side region as an index.

The method for measuring an anti-WT1 antibody of the present invention or various tests using the method can be easily performed by using the polypeptide of the present invention as a measurement reagent. The present invention also provides such a measurement reagent. The measurement reagent can be used as a test reagent (kit) for determining the presence, treatment progress, and prognosis of a WT1-associated disease.

The measurement reagent or the test reagent of the present invention contains the antigen polypeptide of the present invention as an active ingredient. The measurement reagent or the test reagent may further contain arbitrary reagents such as an antibody detection reagent used in the measurement system and reagents necessary for performing the measurement, e.g., an antibody dilution solution, a reaction dilution solution, a buffer solution, a washing solution, and a marker detection reagent.

EXAMPLES

Examples of the present invention will now be described, but the present invention is not limited thereto.

Example 1

1. Material and Method 1-1. Serum Sample

Twenty serum samples of cancer patients collected at Osaka University and commercially available 54 serum samples of healthy subjects were used. Serum of patients treated with a WT1 vaccine was collected before the administration and at several points of time after the administration at Osaka University.

1-2. Measurement of Titer of Antibody to Full-Length WT1 Antigen

The titer of antibody to a full-length WT1 antigen of cancer patient serum was measured by ELISA established by Oji, et al. (Non Patent Document 7: Oji Y, Kitamura Y, Kamino K, et al., WT1 IgG antibody for early detection of nonsmall cell lung cancer and as its prognostic factor, Int J Cancer 2009, 125: 381-7).

1-3. Construction of Partial WT1 Antigen Expression Vector

Full-length WT1 cDNA was divided into an N-terminal region of positions 1-182 (Fr. 1), a central region of positions 181-324 (Fr. 2), and a C-terminal region of positions 294-449 (Fr. 3) of WT1 (SEQ ID NO: 1). These regions were amplified by PCR using Fr. 1 amplification primers (SEQ ID NO: 2 and SEQ ID NO: 3), Fr. 2 amplification primers (SEQ ID NO: 4 and SEQ ID NO: 5), and Fr. 3 amplification primers (SEQ ID NO: 6 and SEQ ID NO: 7). Fr. 1 and Fr. 2 were each cloned into an expression vector pET-42a(+) (Merck KGaA), and Fr. 3 was cloned into an expression vector pQE-80L (QIAGEN N.V.).

```
SEQ ID NO: 2:
ATGCGCGGTACCATGGGCTCCGACGTGCGGGACCTG

SEQ ID NO: 3:
ATGCGCGCGGCCGCCATGGGATCCTCATGCTTGAAT

SEQ ID NO: 4:
ATGCGCGGTACCCCCATGGGCCAGCAGGGCTCGC

SEQ ID NO: 5:
ATGCGCGCGGCCGCCATGAAGGGGCGTTTCTCACTGG

SEQ ID NO: 6:
ATGCGCGGATCCTTCAGAGGCATTCAGGATGTGC

SEQ ID NO: 7:
ATGCGCAAGCTTCAAAGCGCCAGCTGGAGTTTGGTC
```

1-4. Production of Fr. 1 Antigen

The Fr. 1 expression vector was transformed into *E. coli* BL21 (DE3), and expression of recombinant hWT1 Fr. 1 was induced in 1 mM IPTG at 16° C. for 16 hours. The cells were collected by centrifugation, then suspended in D-PBS (−) containing 0.2% Triton X-100, and sonicated, followed by centrifugation to collect the soluble fraction. The soluble fraction was diluted two-fold with D-PBS(−), bound to a GST fusion protein purification column (Glutathione Sepharose HP, GE Healthcare, Inc.) equilibrated with an equilibration buffer solution B1-1 (D-PBS(−) containing 0.1% Triton X-100), washed with the equilibration buffer solution, and then eluted with an elution buffer solution B1-1 (50 mM Tris-HCl, 0.2% Triton X-1001, 10 mM reduced glutathione, pH 8.0). The eluate was further diluted three-fold with an equilibration buffer solution B1-2 (20 mM NaPi, 0.5 M NaCl, 0.2% Triton X-100, pH 7.4), bound to a His-tag purification column (Ni Sepharose HP, GE Healthcare, Inc.) equilibrated with the equilibration buffer solution B1-2, washed with the equilibration buffer solution B1-2 and a washing buffer solution B1-2 (20 mM NaPi, 0.5 M NaCl, 0.2% Triton X-100, 250 mM Imidazole, pH 7.4) sequentially, and then eluted with an elution buffer solution 1-2 (20 mM NaPi, 0.5 M NaCl, 0.2% Triton X-100, 500 mM Imidazole, pH 7.4). The purified Fr. 1 antigen was subjected to protein determination by a Bradford method.

1-5. Preparation of Fr. 2 Antigen

The hWT1 Fr. 2 expression vector was transformed into *E. coli* BL21 (DE3), and expression of a Fr. 2 antigen was induced in 1 mM IPTG at 37° C. for 3 hours. The cells were collected by centrifugation, then suspended in D-PBS(−) containing 0.2% Triton X-100, and sonicated, followed by centrifugation to collect the insoluble fraction. The insoluble fraction was further suspended in D-PBS(−) and was collected by centrifugation. This procedure was repeated twice for washing. The washed insoluble fraction was suspended in D-PBS(−) containing 2 M urea and was incubated at 4° C. for 16 hours. The insoluble fraction was collected by centrifugation and was further suspended in D-PBS(−) containing 6 M urea, followed by incubation at 4° C. for 16 hours to obtain a soluble fraction. The soluble fraction was diluted three-fold with an equilibration buffer solution B2 (20 mM NaPi, 0.5 M NaCl, 6 M urea, 5 mM 2-mercaptoethanol, pH 7.4), bound to a His-tag purification column (Ni Sepharose HP, GE Healthcare, Inc.) equilibrated with an equilibration buffer solution B2, washed with the equilibration buffer solution B2 and a washing buffer solution B2 (20 mM NaPi, 0.5 M NaCl, 6 M urea, 5 mM 2-mercaptoethanol, 200 mM Imidazole, pH 7.4) sequentially, and then eluted with an elution buffer solution B2 (20 mM NaPi, 0.5 M NaCl, 6 M urea, 5 mM 2-mercaptoethanol, 500 mM Imidazole, pH 7.4). The purified Fr. 2 antigen was subjected to protein determination by a Bradford method.

1-6. Preparation of Fr. 3 Antigen

The Fr. 3 expression vector was transformed into *E. coli* BL21 (DE3), and expression of a Fr. 3 antigen was induced in 1 mM IPTG at 16° C. for 16 hours. The cells were collected by centrifugation, then suspended in D-PBS(−) containing 30 μM $ZnCl_2$ and 0.2% Triton X-100, and sonicated, followed by centrifugation to collect the soluble fraction. The soluble fraction was diluted two-fold with an equilibration buffer solution B5 (20 mM Tris-HCl, 1 M NaCl, 0.1% Triton X-100, 30 μM $ZnCl_2$, pH 8.0), bound to a His-tag purification column (TALON superflow, Clontech, Inc.) equilibrated with the equilibration buffer solution, washed with the equilibration buffer solution 5 and a washing buffer solution B5 (10 mM Tris-HCl, 1 M NaCl, 30 μM $ZnCl_2$, 0.1% Triton X-100, 25 mM Imidazole, pH 8.0) sequentially, and then eluted with an elution buffer solution B (10 mM Tris-HCl, 0.72 M NaCl, 30 μM $ZnCl_2$, 0.1% Triton X-100, 200 mM Imidazole, pH 8.0). The purified Fr. 3 antigen was subjected to protein determination by a Bradford method.

1-7. Production of Antigen-Immobilized Solid-Phase Plate

The purified Fr. 1 antigen, Fr. 2 antigen, or Fr. 3 antigen was adjusted to a concentration of 10 μg/mL with D-PBS(−), and 100 μL thereof was added to a 96-well microtiter plate (96-Well EIA/RIA Stripwel Plate, CORNING, Inc.), followed by incubation at 4° C. for 16 hours for immobilization to a solid phase.

The plate was washed with a washing solution (D-PBS(−) containing 0.05% Tween 20) once, and 300 μL of a plate blocking solution (D-PBS(−) containing 1% bovine serum albumin (BSA)) was added to the plate, followed by incubation at 4° C. for 16 hours for blocking. The blocking solution was removed, and the plate was dried in a 25° C. incubator and was then stored at 4° C. until use.

1-8. Measurement of IgG by ELISA Using Fr. 1 Antigen

An antigen-immobilized solid-phase plate was washed with the washing solution once, and 100 μL of a commercially available antibody (hWT1 H-290, SANTA CRUZ Biotechnology, Inc.) or serum appropriately serially diluted with a sample dilution solution 1 (20 mM NaPi, 0.65 M NaCl, 0.05% Tween 20, 0.05% ProClin 300, 1% BSA, pH 8.0) was added to the antigen-immobilized solid-phase plate, followed by a reaction with shaking at 25° C. for 1 hour. Subsequently, the plate was washed with the washing solution three times, and 100 μL of horse-radish peroxidase (HRP)-conjugated Protein G (Acris Antibodies Inc.) diluted 50000-fold with a secondary reaction dilution solution (D-PBS(−) containing 0.05% Tween 20, 0.05% ProClin 300, and 0.5% BSA) was added to the plate, followed by a reaction with shaking at 25° C. for 1 hour. Finally, the plate was washed with the washing solution three times, and 100 μL of 3,3',5,5'-tetramethylbenzidine (TMB) was added to the plate for coloring at room temperature for 10 minutes. The reaction was stopped with 100 μL of 1 N sulfuric acid. The absorbance at 450 nm (reference wavelength: 650 nm) was measured with a microplate reader.

1-9. Measurement of IgG by ELISA Using Fr. 2 Antigen

A GST-expressing *E. coli* extract was added to a commercially available antibody (hWT1 H-290) or serum appropriately serially diluted with the sample dilution solution 1 to give a concentration of 5 μg/mL, and the mixture was subjected to a reaction with shaking at 25° C. for 1 hour to obtain a Fr. 2 sample solution. An antigen-immobilized solid-phase plate was washed with the washing solution once, and 100 μL of the Fr. 2 sample solution was added to the plate, followed by a reaction with shaking at 25° C. for 1 hour. Subsequently, the plate was washed with the washing solution three times, and 100 μL of HRP-conjugated Protein G diluted 50000-fold with the secondary reaction dilution solution was added to the plate, followed by a reaction with shaking at 25° C. for 1 hour. Finally, the plate was washed with the washing solution three times, and 100 μL of TMB was added to the plate for coloring at room temperature for 10 minutes. The reaction was stopped with 100 μL of 1 N sulfuric acid. The absorbance at 450 nm (reference wavelength: 650 nm) was measured with a microplate reader.

1-10. Measurement of IgG by ELISA Using Fr. 3 Antigen

An antigen-immobilized solid-phase plate was washed with the washing solution once, and 100 μL of a commercially available antibody (hWT1 H-290) or serum appropriately serially diluted with a sample dilution solution 2 (20 mM NaPi, 0.05% Tween 20, 0.05% ProClin 300, 1% BSA, pH 8.0) was added to the plate, followed by a reaction with shaking at 25° C. for 1 hour. Subsequently, the plate was washed with the washing solution three times, and 100 μL of HRP-conjugated Protein G diluted 50000-fold with the secondary reaction dilution solution was added to the plate, followed by a reaction with shaking at 25° C. for 1 hour. Finally, the plate was washed with the washing solution three times, and 100 μL of TMB was added to the plate for coloring at room temperature for 10 minutes. The reaction was stopped with 100 μL of 1 N sulfuric acid. The absorbance at 450 nm (reference wavelength: 650 nm) was measured with a microplate reader.

1-11. Measurement of IgM by ELISA Using Each Antigen

IgM antibody was measured as in the measurement of IgG antibody. The detection was performed through a reaction of a 50000-fold diluted HRP-conjugated anti-human IgM specific antibody.

2. Results 2-1. Titer of Antibody to Full-Length WT1 Antigen

Figure 1:
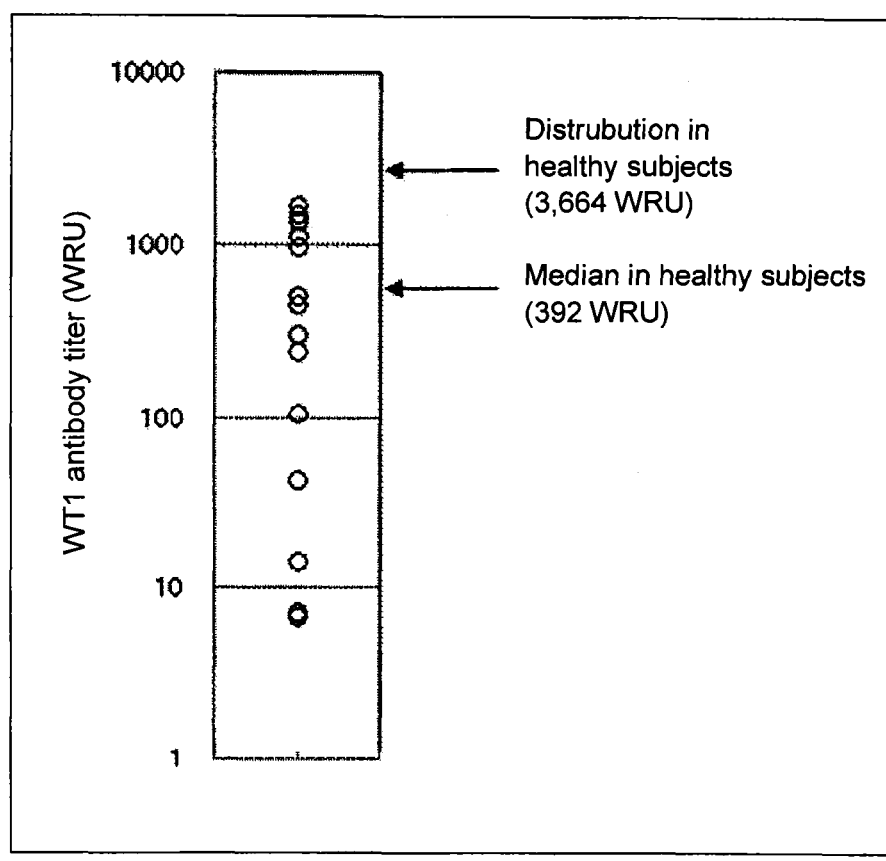
FIG. 1 is a graph showing the titers of antibody against a full-length WT1 antigen in blood of cancer patients.

Table 1 and FIG. 1 show the blood anti-WT1 antibody titers of cancer patient serum samples measured by the method of Oji, et al. According to the report by Oji, et al., the titer distribution of antibodies against the full-length WT1 antigen in healthy subjects is 10 to 3664 WRU, and the median thereof is 392 WRU (Non Patent Document 7). The titer distribution of antibodies in 20 cancer patient serum samples used in this test was 7 to 1682 WRU. Thus, all the samples were within the range of healthy subjects.

TABLE 1

| No. | WT1 antibody titer (WRU) | Fr. 1 antibody titer (unit) | Fr. 2 antibody titer (unit) | Fr. 3 antibody titer (unit) |
|---|---|---|---|---|
| 1 | 102 | 1.9 | 54.4 | 367.9 |
| 2 | 42 | 4.5 | 22.2 | 258.5 |
| 3 | 103 | 5.2 | 74.4 | 184.7 |
| 4 | 103 | 3.7 | 78.7 | 485.2 |
| 5 | 14 | 4.0 | 9.4 | 73.8 |
| 6 | 968 | 8.7 | 134.5 | 5045.1 |
| 7 | 242 | 9.2 | 49.8 | 253.4 |
| 8 | 1143 | 8.6 | 154.4 | 5391.5 |
| 9 | 242 | 21.0 | 43.2 | 580.2 |
| 10 | 1682 | 29.9 | 229.9 | 9087.8 |
| 11 | 453 | 7.1 | 69.9 | 1029.6 |
| 12 | 237 | 5.2 | 42.2 | 337.8 |
| 13 | 499 | 6.2 | 56.2 | 559.9 |
| 14 | 1389 | 21.2 | 166.9 | 7887.0 |
| 15 | 984 | 19.3 | 204.9 | 8326.8 |
| 16 | 7 | 1.6 | 10.0 | 47.5 |
| 17 | 14 | 2.8 | 14.9 | 115.2 |
| 18 | 1524 | 11.8 | 150.4 | 7826.5 |
| 19 | 42 | 2.1 | 10.0 | 208.6 |
| 20 | 306 | 6.8 | 104.0 | 784.7 |

2-2. Titer of Antibody to Partial WT1 Antigen in Cancer Patient

Blood antibody titers were measured by ELISA using partial WT1 antigens. The blood antibody titers were calculated from a calibration curve of absorbance versus concentration constructed using a serially diluted commercially available antibody as a standard. The titers of antibody against each antigen in blood of cancer patients are shown in Table 1.

Figure 2:
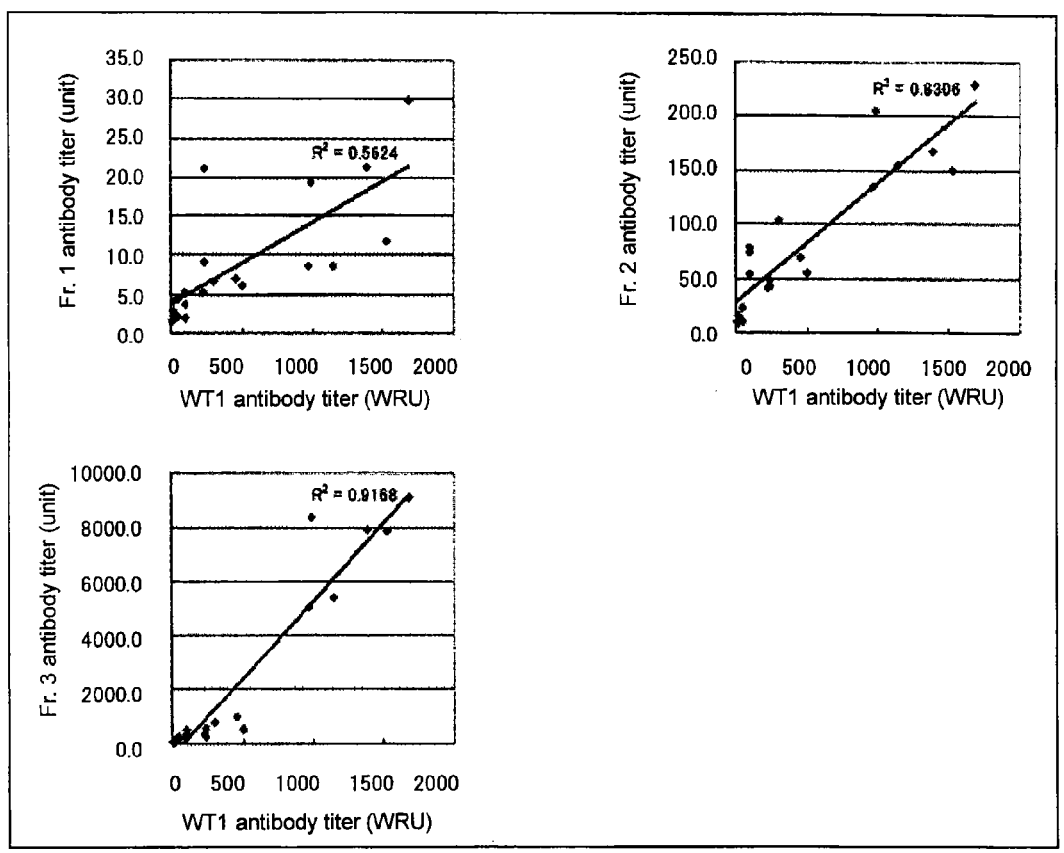
FIG. 2 includes graphs showing comparison between the titer of antibody against the full-length WT1 antigen and the titers of antibody against partial WT1 antigens, i.e., the results of comparison of the titer of antibody against the full-length WT1 antigen to the titer of antibody against a Fr. 1 antigen (a), a Fr. 2 antigen (b), and a Fr. 3 antigen (c), with the vertical axis showing the titer (unit) of antibody against a partial WT1 antigen and the horizontal axis showing the titer (WRU) of antibody against a full-length WT1 antigen.
Figure 3:
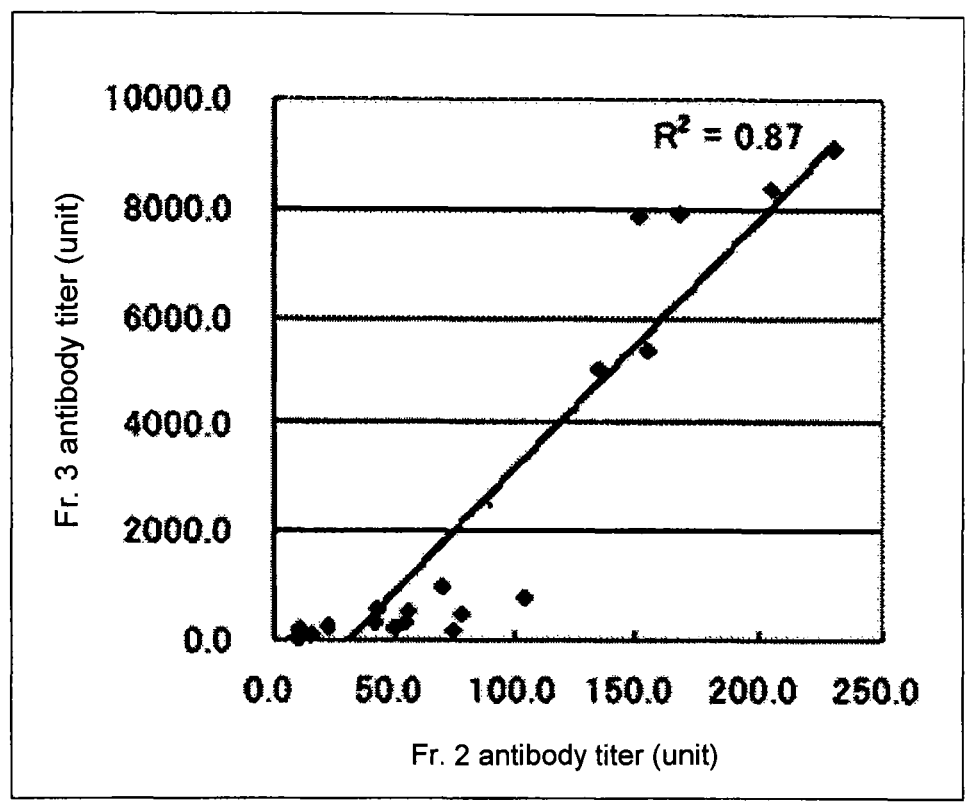
FIG. 3 is a graph showing comparison between the titer of antibody against the Fr. 2 antigen and the titer of antibody against the Fr. 3 antigen, with the vertical axis showing the titer (unit) of antibody against the Fr. 3 antigen and the horizontal axis showing the titer (WRU) of antibody against the Fr. 2 antigen.

FIG. 2 shows the results of comparison between the titers of antibodies against each partial WT1 antigen and the full-length WT1 antigen. The titers of antibodies against the Fr. 2 antigen and the Fr. 3 antigen showed high correlations with the titer of antibody against the full-length WT1 antigen. The correlation between the titer of antibody against the Fr. 2 antigen and the titer of antibody against the Fr. 3 antigen was also high (FIG. 3).

These results suggest that the titer of antibody against the full-length WT1 antigen reflects the titer of antibody against Fr. 3 and that Fr. 3 includes a major epitope to the antibody in blood.

2-3. Titer Distribution of Antibody Against Partial WT1 Antigen

Figure 4:
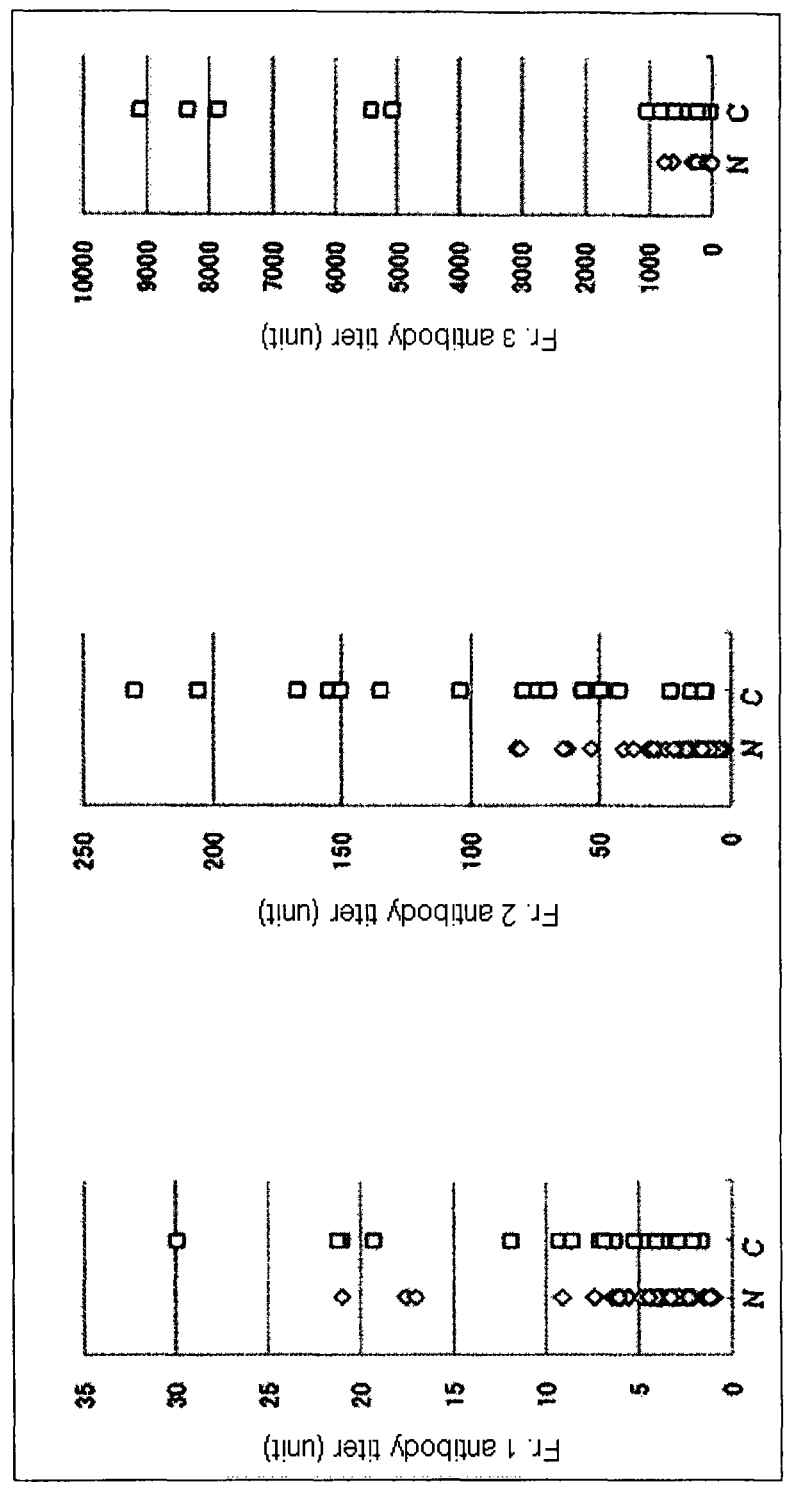
FIG. 4 is a graph showing the titer distribution of antibodies against partial WT1 antigens, i.e., the titer distribution of antibodies against partial WT1 antigens in healthy subjects and cancer patients, wherein N and C respectively show the distribution in 54 healthy subjects and the distribution in 20 cancer patients against the Fr. 1 antigen (a), the Fr. 2 antigen (b), and the Fr. 3 antigen (c).

FIG. 4 shows the results of comparison between the titer distribution of antibodies against partial WT1 antigens in 54 healthy subjects (N) and the titer distribution of antibodies against partial WT1 antigens in 20 cancer patients (C). The titer distributions of antibodies against the Fr. 2 antigen and the Fr. 3 antigen in the cancer patients were higher than those in the healthy subjects, whereas the titer distributions of antibodies against the Fr. 1 antigen were substantially the same in the cancer patients and the healthy subjects. In particular, the titer distribution of antibodies against the Fr. 3 antigen was most broad, and the antibody titers of six cancer patient samples were five or more times higher than those of the healthy subjects.

The results above demonstrate that the Fr. 3 antigen can classify a high titer group more clearly than the case using the titer of antibody against the full-length WT1 antigen.

Example 2

Antigen Inhibition Test

In order to investigate the phenomenon that the titer of antibody against the Fr. 3 antigen is detected with higher sensitivity compared to the titer of antibody against the full-length WT1 antigen, whether the antibody epitope of the Fr. 3 antigen is masked by reacting the Fr. 1 antigen or Fr. 2 antigen to the Fr. 3 antigen was investigated. As the samples, a polyclonal antibody (PoAb) against Fr. 3 and the serum of three patients (sample Nos. 3, 7, and 9) having high titers of antibody against Fr. 3 were used.

1. Method

A Fr. 3 antigen-immobilized solid-phase plate was washed with the washing solution once, and 100 µL, of the Fr. 1 antigen or Fr. 2 antigen diluted with the secondary reaction dilution solution was added to the plate, followed by a reaction with shaking at 25° C. for 1 hour. Subsequently, 100 µL of a commercially available antibody (hWT1 C-19, SANTA CRUZ Biotechnology, Inc.) or serum diluted with the sample dilution solution 1 was added to the plate, followed by a reaction with shaking at 25° C. for 1 hour. Furthermore, the plate was washed with the washing solution three times, and then 100 µL of HRP-conjugated Protein G diluted 50000-fold with the secondary reaction dilution solution was added to the plate, followed by a reaction with shaking at 25° C. for 1 hour. Finally, the plate was washed with the washing solution three times, and 100 µL of TMB was added to the plate for coloring at room temperature for 10 minutes. The reaction was stopped with 100 µL of 1 N sulfuric acid. The absorbance at 450 nm (reference wavelength: 650 nm) was measured with a microplate reader, and the reaction inhibition rate (B/B0) was calculated assuming that the value in the absence of the antigen was 100%.

2. Results

Figure 5:
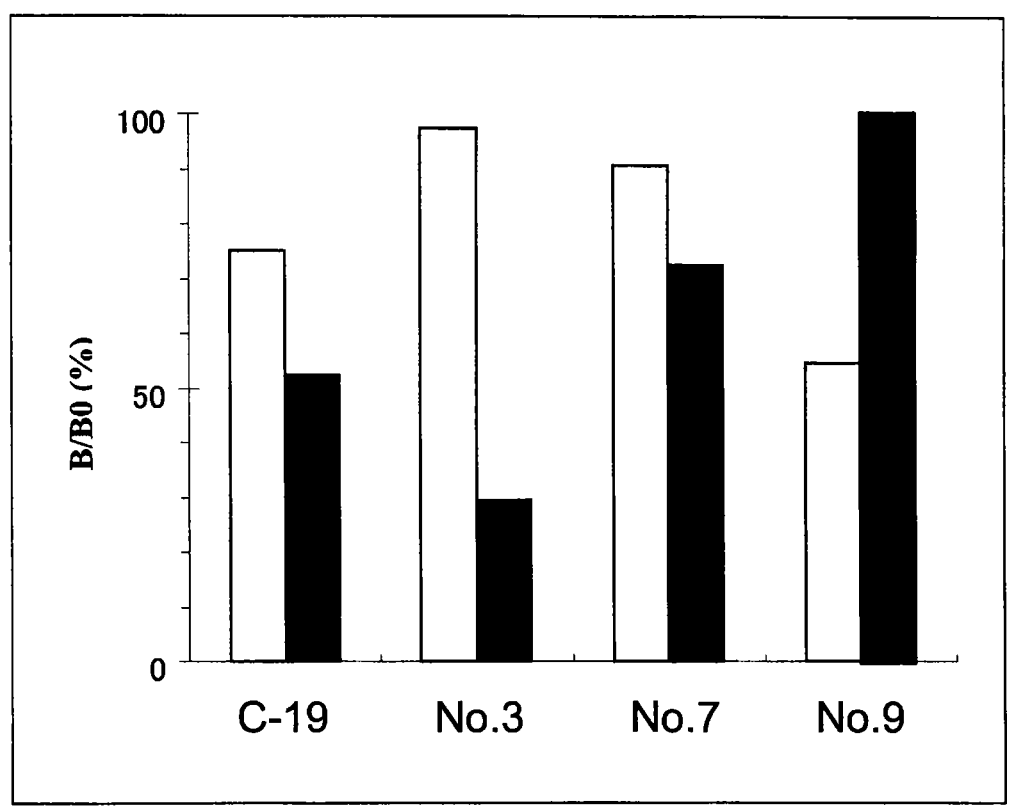
FIG. 5 is a graph showing the results of an antigen inhibition test against the Fr. 3 antigen, i.e., the results that the reactivity of the antibody to Fr. 3 is inhibited by Fr. 1 and Fr. 2, wherein C-19 is a polyclonal antibody against the Fr.

The results are shown in FIG. 5.

Fr. 1 and Fr. 2 inhibited the reactivity of PoAb to Fr. 3 by 25% and 50%, respectively. Similarly, Fr. 1 or Fr. 2 inhibited the antibody titer of each serum sample to Fr. 3. In sample No. 3, the reaction was not inhibited by Fr. 1, but 70% thereof was inhibited by Fr. 2. In sample No. 9, the reaction was not inhibited by Fr. 2, but 40% thereof was inhibited by Fr. 1. In sample No. 7, though the degrees were low, the reaction was inhibited by both Fr. 1 and Fr. 2 by 10% and 20%, respectively.

The results above suggest that Fr. 1 and Fr. 2 have capability of binding to Fr. 3 and that the binding masks the antibody epitope of Fr. 3.

Example 3

Evaluation of Antibody Titer in Brain Tumor Patient Administered with WT1 Vaccine The titers of IgG and IgM antibodies against the Fr. 1 antigen, Fr. 2 antigen, and Fr. 3 antigen of patients administered with a modified WT1 235 peptide vaccine (amino acid sequence (YTWNQMNL)) were evaluated. As the patient samples, five samples of the stable disease (SD) group and four samples of the progression disease (PD) group were used. The cancer tissues were evaluated by MRI.

FIG. 6 summarizes the changes in IgG antibody titer of patients administered with the WT1 235 peptide.

The titer of IgG antibody against Fr. 1 was hardly detected in all patients. The titers of antibody against Fr. 3 were obviously classified into a high value group and a low value group and hardly changed before and after the administration. In addition, these antibody titers substantially did not show a correlation with the full-length WT1 antigen. However, the titer of antibody against Fr. 2 increased with time after vaccination in some patients. This antibody titer was confirmed to have a high correlation with the titer of antibody against the full-length WT1 antigen.

FIG. 7 summarizes the results of comparison of the titer of IgG antibody against each antigen before vaccination and therapeutic response.

The results show that the titers of antibody against Fr. 3 were 100 units or more in four of five samples of the SD group and that the antibody titers were less than 100 units in all four samples of the PD group. Such tendencies were not recognized in the titers of antibodies against other antigens. The results above show that patients having high titers of IgG antibody against Fr. 3 before vaccination are patients who respond to the vaccine therapy.

FIG. 8 summarizes the results of comparison of the titer of IgG antibody against each antigen after vaccination and therapeutic response. The results show that the titers of antibodies against Fr. 2 and the full-length WT1 antigen at three months after vaccination were two-fold or more higher than those before vaccination in three of five samples of the SD group, whereas the antibody titers in all four samples of the PD group hardly increased. The results above show that patients having increased titers of IgG antibody against Fr. 2 after vaccination are patients who respond to the vaccine therapy.

The titers of IgM antibodies against Fr. 2 and Fr. 3 were evaluated using samples before vaccination. FIG. 9 summarizes the results of comparison of IgM antibody titer and therapeutic response. The results show that the titers of antibody against Fr. 2 were 200 units or more in all five samples of the SD group and that the antibody titers were less than 200 units in all four samples of the PD group. In addition, the titers of antibody against Fr. 3 were 80 units or more in three of five samples of the SD group, and the antibody titers were less than 80 units in all four samples of the PD group. The results above show that patients having high titers of IgM antibodies against Fr. 2 and Fr. 3 before vaccination are patients who respond to the vaccine therapy.

Example 4

Evaluation of Antibody Titer in Colon Cancer Patient Administered with WT1 Vaccine The titers of IgG and IgM antibodies against each antigen in patients administered the WT1 235 peptide were evaluated using eight samples of the SD group and 14 samples of the PD group as patient samples. The titers of antibodies against Fr. 2 and Fr. 3 were evaluated using samples before the vaccination. The results are summarized in FIG. 10.

The titers of IgG and IgM antibodies against Fr. 3 in the SD group were obviously higher than those in the PD group. The titers of antibody against Fr. 3 were 140 units or more in four of eight samples of the SD group, whereas the antibody titer was 140 units or less in all 14 samples of the PD group. The titers of IgM antibody against Fr. 3 were 140 units or more in six of eight samples of the SD group, whereas the antibody titers were 140 units or less in 10 of 14 samples of the PD group. The results above show that patients having high titers of IgM and IgG antibodies against Fr. 3 before vaccination are patients who respond to the vaccine therapy.

Example 5

Stratification of Responders to WT1 Vaccine Therapy Before Therapy

The results of evaluation of the titers of IgM and IgG antibodies against each antigen show that the titer of antibody against Fr. 3 before vaccination is associated with the therapeutic response in both brain tumor patients and colon cancer patients. Accordingly, the titers of IgM and IgG antibodies against Fr. 3 before vaccination were summarized in brain tumor patients and in colon cancer patients separately. The results of brain tumor patients are shown in FIG. 11.

In the brain tumor patients, when 100 units are prescribed as reference values of the IgG antibody titer and the IgM antibody titer, either IgM or IgG antibody titer was equal to or higher than the reference value in all samples of the SD group, whereas both IgM and IgG antibody titers were equal to or lower than the reference values in all samples of the PD group, which allows stratification. That is, the sensitivity and specificity in selection of responders before vaccination are both 100%. The results of colon cancer patients are shown in FIG. 12. When 150 units are prescribed as reference values of the IgG antibody titer and the IgM antibody titer, either IgM or IgG antibody titer was equal to or higher than the reference value in seven of eight samples of the SD group, whereas both IgM and IgG antibody titers were equal to or lower than the reference values in 10 of 14 samples of the PD group, which allows stratification. That is, the sensitivity and specificity in selection of responders before vaccination are 85% and 71%, respectively.

The results above demonstrate that stratification before therapy of responders to the therapy is possible even in different cancer types by measuring the titers of IgM and IgG antibodies against Fr. 3 before vaccination.

The invention claimed is:

1. A method for detecting an anti-WT1 antibody in a sample, comprising:
   contacting a sample with a polypeptide having antigenicity to the anti-WT1 antibody, wherein the
   polypeptide consists of the amino acid sequence of positions 294-449 in SEQ ID NO: 1; and
   detecting a concentration of the anti-WT1 antibody in the sample.

2. The method according to claim 1, wherein the detecting comprises
   immobilizing the polypeptide to a solid phase; and
   detecting a reaction product between the immobilized polypeptide and an anti-WT1 antibody present in the sample to measure a concentration of the anti-WT1 antibody.

3. The method according to claim 1, wherein the detecting of the concentration of the anti-WT1 antibody comprises performing one of radioimmunoassay, enzyme immunoassay, fluoroimmunoassay, indirect fluorescence assay, luminescent immunoassay, physicochemical assay, and Western blotting.

4. The method according to claim 1, wherein the detecting of the concentration of the anti-WT1 antibody comprises performing ELISA.

5. A method for detecting a WT1-associated disease, comprising:
   contacting a sample from a subject with a polypeptide having antigenicity to an anti-WT1 antibody,
   wherein the polypeptide consists of the amino acid sequence of positions 294-449 in SEQ ID NO: 1;
   and detecting the anti-WT1 antibody in the subject.

6. The method according to claim 5, wherein the WT1-associated disease is leukemia.

7. A method for predicting a responder to or for therapeutic monitoring of WT1 vaccine therapy of cancer, comprising:
   contacting a sample from a subject with a polypeptide having antigenicity to an anti-WT1 antibody,
   wherein the polypeptide consists of the amino acid sequence of positions 294-449 in SEQ ID NO: 1; and
   detecting the anti-WT1 antibody in the subject.

8. The method according to claim 7, wherein the cancer is brain tumor or colon cancer.

9. A method of detecting immune response ability of a subject in a WT1-associated disease, comprising:
   detecting an anti-WT1 antibody in a sample taken from a subject having a WT1-associated disease by the method according to claim 1,
   wherein presence of the anti-WT1 antibody indicates the subject's ability to show immune response.

10. The method according to claim 9, wherein the WT1-associated disease is leukemia.

* * * * *

SEQUENCE LISTING

```
<160> NUMBER OF SEQ ID NOS: 7

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270
```

Ser Asp Asn His Thr Thr Pro Ile Leu Cys Gly Ala Gln Tyr Arg Ile
    275                 280                 285

His Thr His Gly Val Phe Arg Gly Ile Gln Asp Val Arg Arg Val Pro
290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
            435                 440                 445

Leu

<210> SEQ ID NO 2
<211> LENGTH: 36
<212> TYPE: DNA
<213> ORGANISM: Artificial
<220> FEATURE:
<223> OTHER INFORMATION: primer sequence specific to WT1 gene(Fr.1)

<400> SEQUENCE: 2
atgcgcggta ccatgggctc cgacgtgcgg gacctg                           36

<210> SEQ ID NO 3
<211> LENGTH: 36
<212> TYPE: DNA
<213> ORGANISM: Artificial
<220> FEATURE:
<223> OTHER INFORMATION: primer sequence specific to WT1 gene(Fr.1)

<400> SEQUENCE: 3
atgcgcgcgg ccgccatggg atcctcatgc ttgaat                           36

<210> SEQ ID NO 4
<211> LENGTH: 34
<212> TYPE: DNA
<213> ORGANISM: Artificial
<220> FEATURE:
<223> OTHER INFORMATION: primer sequence specific to WT1 gene(Fr.2)

<400> SEQUENCE: 4
atgcgcggta ccccccatggg ccagcagggc tcgc                            34

<210> SEQ ID NO 5
<211> LENGTH: 37
<212> TYPE: DNA
<213> ORGANISM: Artificial
<220> FEATURE:
<223> OTHER INFORMATION: primer sequence specific to WT1 gene(Fr.2)

```
<400> SEQUENCE: 5
atgcgcgcgg ccgccatgaa ggggcgtttc tcactgg                                37

<210> SEQ ID NO 6
<211> LENGTH: 34
<212> TYPE: DNA
<213> ORGANISM: Artificial
<220> FEATURE:
<223> OTHER INFORMATION: primer sequence specific to WT1 gene(Fr.3)

<400> SEQUENCE: 6
atgcgcggat ccttcagagg cattcaggat gtgc                                   34

<210> SEQ ID NO 7
<211> LENGTH: 36
<212> TYPE: DNA
<213> ORGANISM: Artificial
<220> FEATURE:
<223> OTHER INFORMATION: primer sequence specific to WT1 gene(Fr.3)

<400> SEQUENCE: 7
atgcgcaagc ttcaaagcgc cagctggagt ttggtc                                 36
```